United States Patent
Ponsi et al.

(10) Patent No.: US 8,535,255 B2
(45) Date of Patent: Sep. 17, 2013

(54) THERAPEUTIC BOOTS STABILIZATION WEDGE

(75) Inventors: Lawrence G. Ponsi, Wheeling, IL (US); Jeffrey K. Crum, Wonder Lake, IL (US)

(73) Assignee: Sage Products, Inc., Cary, IL (US)

(*) Notice: Subject to any disclaimer, the term of this patent is extended or adjusted under 35 U.S.C. 154(b) by 471 days.

(21) Appl. No.: 11/855,560

(22) Filed: Sep. 14, 2007

(65) Prior Publication Data

US 2009/0076427 A1 Mar. 19, 2009

(51) Int. Cl.
- *A61F 13/00* (2006.01)
- *A61F 5/37* (2006.01)
- *A61G 15/00* (2006.01)

(52) U.S. Cl.
USPC ............ 602/62; 602/60; 602/61; 128/845; 128/882

(58) Field of Classification Search
USPC ............ 602/19, 20, 23, 53, 60–65, 66, 21, 602/5, 26–27; 128/845, 878, 879, 882; 5/630, 5/646, 647, 648, 650, 651; 36/110, 88–90
See application file for complete search history.

(56) References Cited

U.S. PATENT DOCUMENTS

| | | | |
|---|---|---|---|
| 3,913,243 A | 10/1975 | Arnold et al. | |
| 4,135,504 A | 1/1979 | Spann | |
| 4,745,917 A | 5/1988 | Hasty et al. | |
| 4,924,605 A | 5/1990 | Spademan | |
| 5,046,487 A | 9/1991 | Scott | |
| 5,832,632 A | 11/1998 | Bergeron | |
| 5,921,949 A * | 7/1999 | Dray | 602/64 |
| 6,120,472 A * | 9/2000 | Singer, Jr. | 602/64 |
| 6,182,311 B1 | 2/2001 | Buchanan et al. | |
| 6,585,674 B2 * | 7/2003 | Toda | 602/62 |
| 8,152,749 B2 | 4/2012 | Ponsi et al. | |
| 2009/0084390 A1 | 4/2009 | Davis et al. | |

OTHER PUBLICATIONS

U.S. Patent and Trademark Office's Office Action dated Jul. 20, 2012 for U.S. Appl. No. 13/242,132.

* cited by examiner

*Primary Examiner* — Kim M Lewis
(74) *Attorney, Agent, or Firm* — Brinks Hofer Gilson & Lione

(57) ABSTRACT

A device for stabilizing a limb, typically when the limb is in a therapeutic boot. A wedge-shaped stabilization block includes an outwardly-extending tether. A fastener in the form of spaced fastener elements is located on the tether for securing the stabilization block in place.

17 Claims, 4 Drawing Sheets

THERAPEUTIC BOOTS STABILIZATION WEDGE

BACKGROUND OF THE INVENTION

This invention relates to stabilization of a limb in a patient setting, and in particular to a device for use as an adjunct for limb stabilization.

In co-pending U.S. patent application Ser. No. 11/240,679 filed Sep. 30, 2005 and assigned to the assignee of the present application, a heel ulcer prevention and cushioning boot is disclosed and described. The boot provides heel support and comfort, as well as proper positioning of a patient's leg to avoid creating other problems, such as ulcers.

Sometimes, for whatever reasons, including inability of the patient to maintain proper orientation of a limb, the heel ulcer and cushioning boot may need additional stabilization to maintain the proper limb orientation. The present invention provides that additional stabilization.

SUMMARY OF THE INVENTION

The invention is directed to a device for stabilizing a limb, comprising a stabilization block, a tether secured to and extending from the block, and a fastener for securing the stabilization block in place for supporting the limb.

In accordance with one form of the invention, the stabilization block is elongated and generally triangular in cross-section. The tether comprises an elongated strap, with the fastener comprising a pair of spaced fastener elements on the strap. In one form of the invention, the fastener elements comprise hook-and-loop fasteners which are located substantially at opposite ends of the strap, with one located proximate the block and the other located at the opposite end of the tether.

In another form of the invention, a pair of stabilization blocks is provided, with the blocks being spaced apart and with the tether extending between and secured to the respective blocks.

BRIEF DESCRIPTION OF THE DRAWINGS

The invention is described in greater detail in the following description of examples embodying the best mode of the invention, taken in conjunction with the drawing figures, in which.

DESCRIPTION OF EXAMPLES EMBODYING THE BEST MODE OF THE INVENTION

Figure 1:
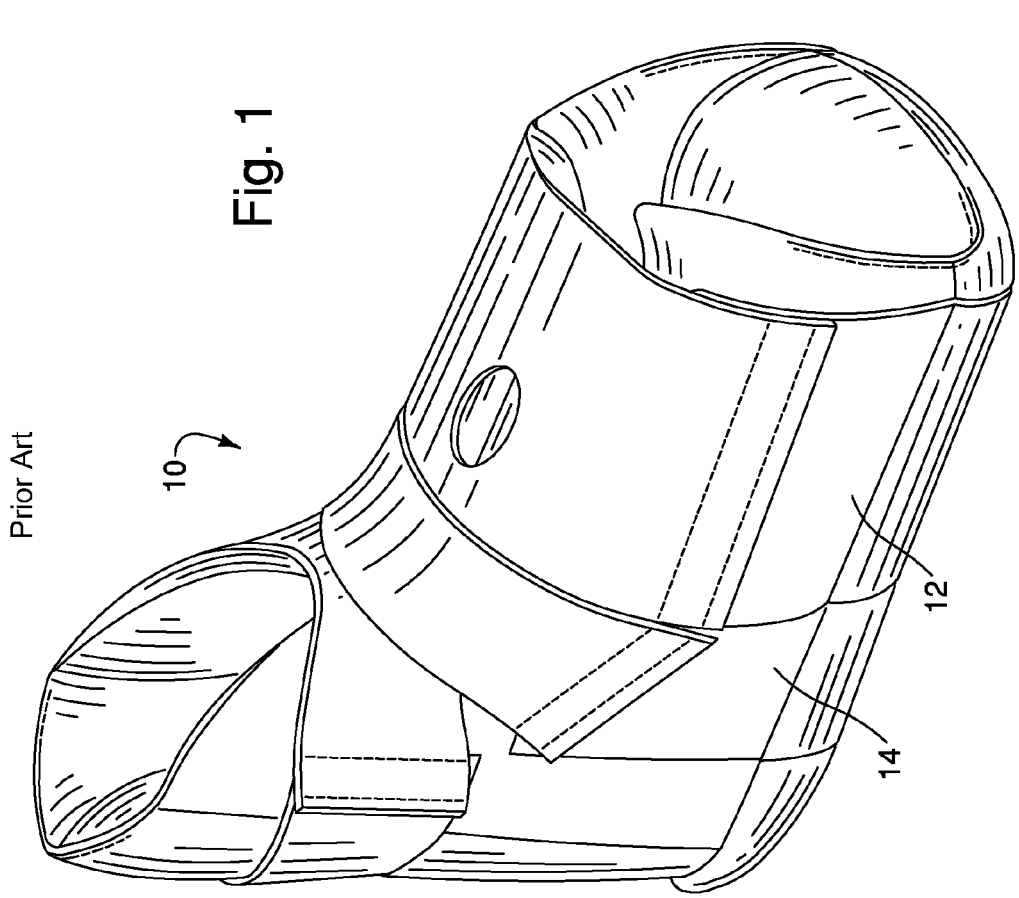
FIG. 1 is a perspective view of a therapeutic boot for which the invention of the present application is particularly suitable.

The stabilization wedge according to the invention is particularly suitable for use in combination with a therapeutic boot, such as the boot 10 illustrated in FIG. 1. The boot 10 is described in greater detail in co-pending U.S. patent application Ser. No. 11/240,679, filed Sep. 30, 2005, the disclosure of which is incorporated herein by reference. Greater detail can be obtained from that application. Of the many features of the boot 10, hook-and-loop fastener segments 12 and 14 are particularly useful in combination with the stabilization wedge of the present invention, as will become evident from the description below.

Figure 2:
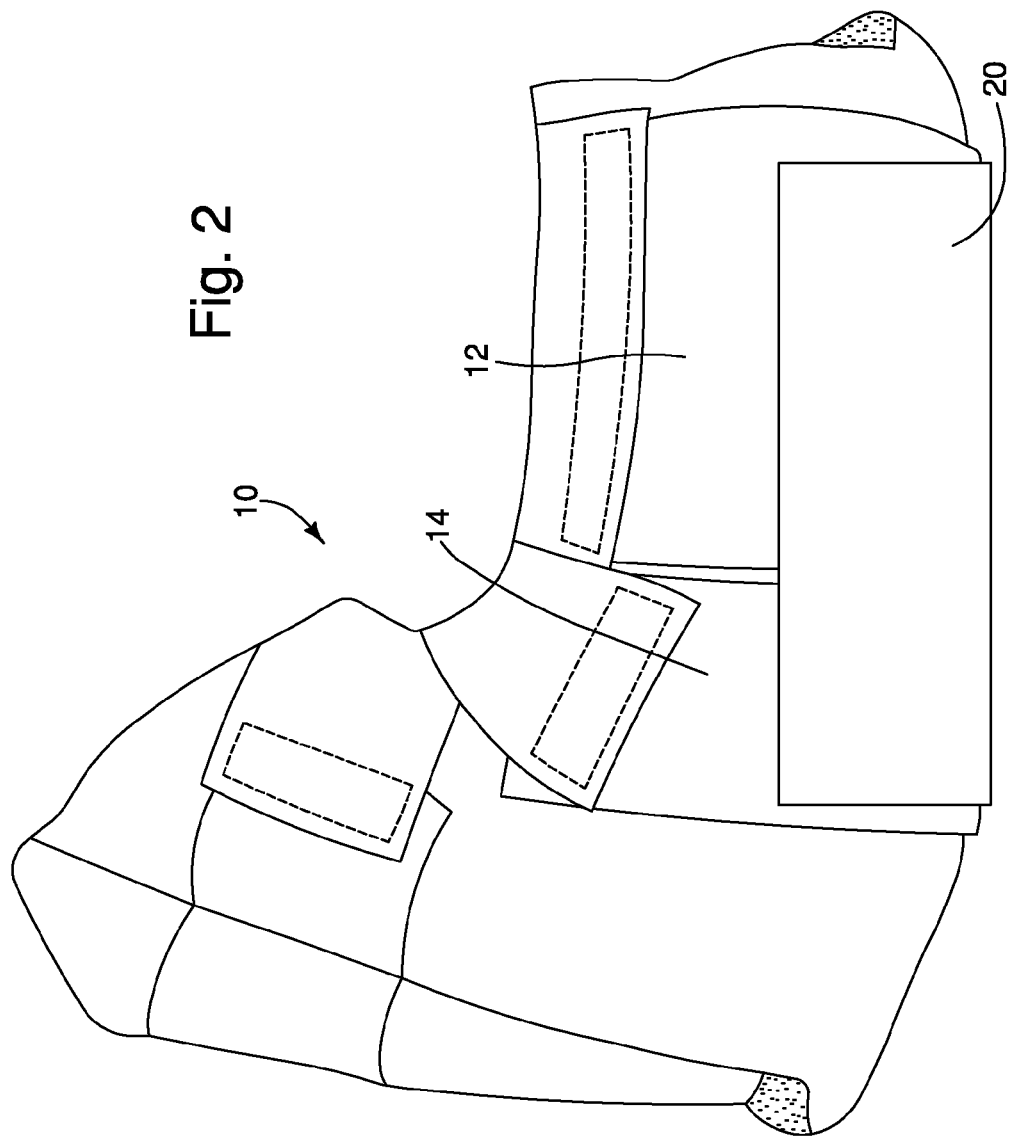
FIG. 2 is an elevational view of the boot of FIG. 1, having the stabilization wedge of the invention in place.
Figure 3:
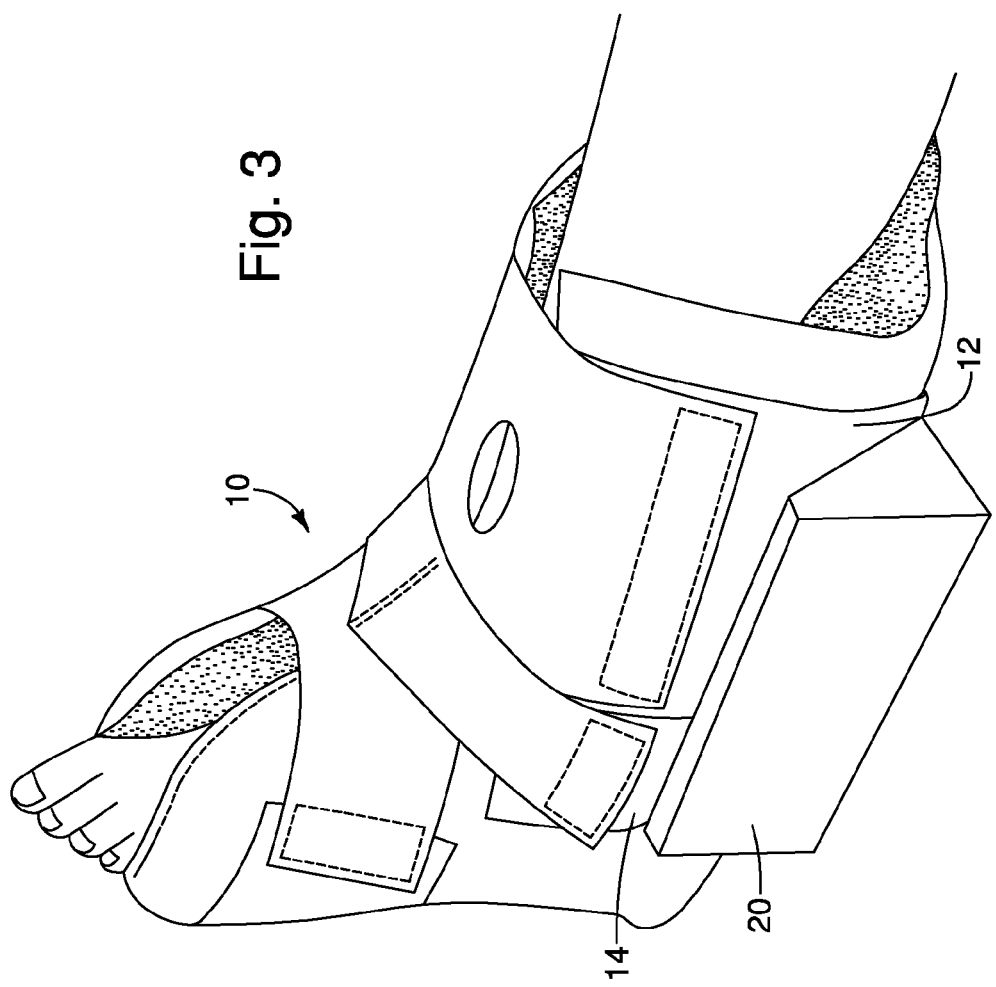
FIG. 3 is a perspective view similar to FIG. 1, with the stabilization wedge in place and showing how a patient's leg is supported.
Figure 4:
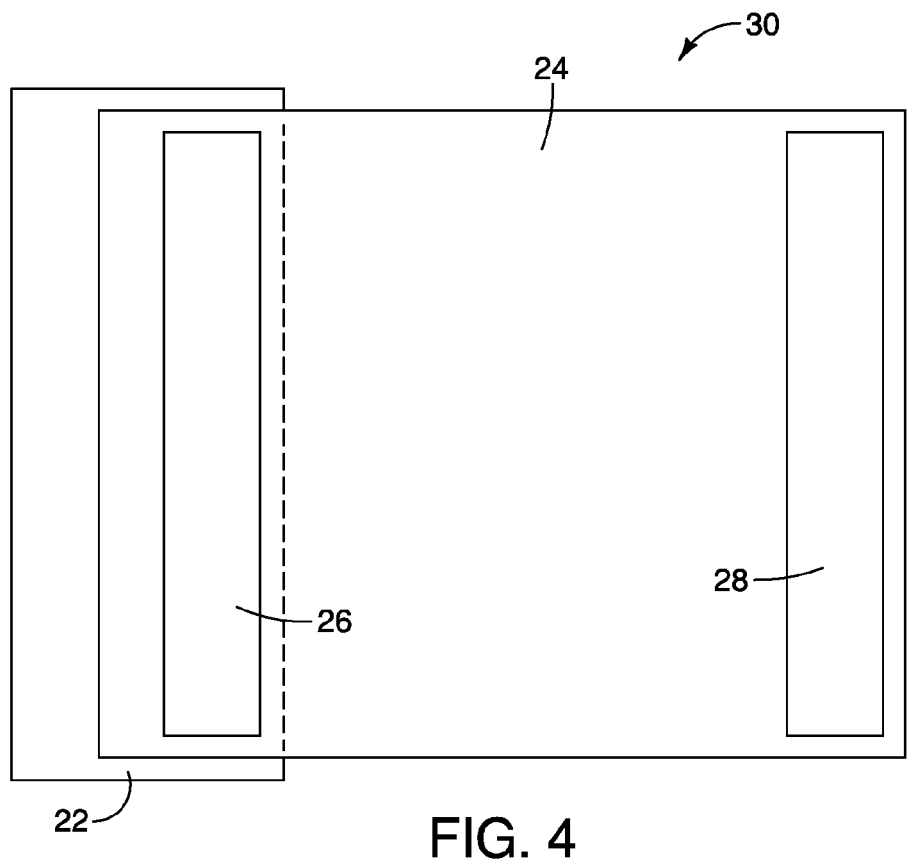
FIG. 4 is a top plan view of the stabilization wedge.
Figure 5:
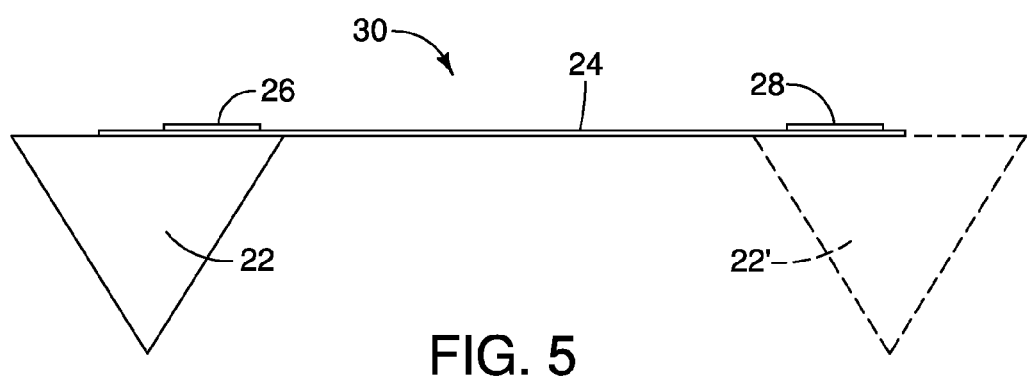
FIG. 5 is an elevational view of the wedge of FIG. 4.

The stabilization wedge of one form of the invention is shown in FIGS. 2 and 3, with a slightly different form shown in FIGS. 4 and 5. The wedge 20 shown in FIGS. 2 and 3 differs from the wedge 22 shown in FIGS. 4 and 5 only in the particular cross-sectional configuration. As shown in FIG. 3, the wedge 20 is generally trapezoidal in cross-section, while the wedge 22 shown in FIGS. 4 and 5 is generally triangular in cross section. Other shapes of the wedges 20 and 22 will be apparent to one skilled in the art, and the invention is not limited to simply a trapezoidal or triangular cross-section.

No matter the cross-section of the wedge 20 or 22, the wedge comprises a stabilization block, and has a tether secured to and extending from the stabilization block. The tether preferably comprises an elongated strap 24, and may be secured to the respective wedge 20 or 22 by any means, such as sonic welding, adhesives, or any other means of forming a permanent connection between the wedge 20 or 22 and the elongated strap 24. The strap 24 is preferably quite flexible, and can be made of any suitable material, such as plastic or fabric. The wedge 20 or 22, on the other hand, is substantially rigid, and can be formed of any suitable material, such as high density foam, plastic or the like.

As shown in the drawing figures, the wedges 20 and 22 are elongated and for fastening to the boot 10, a fastener is provided in the form of a pair of spaced fastener elements 26 and 28 on the strap 24. The fastener elements 26 and 28 complement the fastener segments 12 and 14, thus one of the segments 12 and 14 or elements 26 and 28 is preferably a hook element, while the other of the fastener segments 12 and 14 and fastener elements 26 and 28 is a loop element. Thus, when the wedge 20 or 22 is applied to the boot 10 as illustrated in the drawing figures, the hook and loop elements engage and hold the wedge 20 or 22 in place.

As illustrated, the fastener elements 26 and 28 are located substantially at opposite ends of the strap 24. The spacing of the fastener elements 26 and 28 is such to advantageously engage the fastener segments 12 and 14. As illustrated, the fastener element 26 is located proximate the stabilization wedge 20 or 22, and the fastener element 28 is located on the elongated strap 24 opposite the fastener element 26.

While the fastener elements 26 and 28 are preferably hook-and-loop fastener segments to advantageously engage the hook-and-loop fastener segments 12 and 14, other types of fastener elements can be employed, as will be evident to one skilled in the art. Permanent fasteners, such as adhesives, can be utilized, as well as other types of temporary connection to the boot, such as various kinds of fasteners. The type of connection will be dictated by whether the user wishes a more permanent type of connection, or a readily removable type of connection.

As is evident, the stabilization wedge 20 or 22 can be used on either side of the boot 10. If need be, the wedges 20 or 22 can be doubled, that is, instead of a single wedge proximate the fastener element 26, there can be a second wedge, such as the wedge 22', proximate the fastener element 28. Thus, both sides of the boot 10 can be stabilized if needed.

The shape of the wedge 20 or 22 can vary depending upon the nature of the boot 10 and the use in connection with the boot. While two types of wedges 20 and 22 have been illustrated and described, it will be evident that other shapes will perform the stabilization functions as explained.

Various changes can be made to the invention without departing from the spirit thereof or scope of the following claims.

What is claimed is:

1. A device for stabilizing a limb, comprising:
   a. a cushioned therapeutic boot comprising a leg engaging portion, a foot engaging portion, and a leg-accepting aperture extending along a front side of the side boot,
   b. a stabilization block,
   c. a tether, said tether having an end secured to said block and said tether extending from said block, and
   d. a fastener means for securing the stabilization block in place on the boot for stabilizing the limb, with said block being located on one side of said tether and said fastener means being located on an opposite side of said tether.

2. The device according to claim 1, in which said stabilization block is elongated and generally trapezoidal in cross-section.

3. The device according to claim 1, in which said stabilization block is elongated and generally triangular in cross-section.

4. The device according to claim 1, in which said tether comprises an elongated strap.

5. The device according to claim 4, including a second fastener on said strap.

6. The device according to claim 5, in which said fasteners comprise hook-and-loop elements.

7. The device according to claim 5, in which said fasteners are located substantially at opposite ends of said strap.

8. The device according to claim 4, in which said strap is adhesively secured to said block.

9. The device according to claim 1, including a pair of said stabilization blocks, said blocks being spaced with said tether extending between and secured to said blocks.

10. The device for stabilizing a limb, comprising:
    a. a cushioned therapeutic boot comprising a leg engaging portion, a foot engaging portion, and a leg-accepting aperture extending along a front side of the said boot,
    b. a raised stabilization block,
    c. a tether, said tether having an end secured to said block and said tether extending from said block,
    d. a fastener for securing the stabilization block in place for stabilizing the limb, said fastener being located on said tether at said stabilization block, with said block being located on one side of said tether and said fastener being located on an opposite side of said tether, and
    e. including a pair of said fasteners, said fasteners being spaced from one another.

11. The device according to claim 10, in which one of said fasteners of said fasteners is located at said block and the other of said fasteners is located on said tether opposite the first of said fasteners.

12. The device according to claim 11, in which one of said fasteners is located proximate said block and the other of said fasteners is located on said tether opposite the first of said fasteners.

13. A device for stabilizing a limb, comprising:
    a. a cushioned therapeutic boot comprising a leg engaging portion, a foot engaging portion, and a leg-accepting aperture extending along a front side of said boot,
    b. an elongated, raised stabilization block,
    c. an elongated strap, said strap having one end secured to said block, said strap extending from said block, and said strap configured to be coupled with the boot, and
    d. a pair of fasteners positioned on said strap for securing the stabilization block in place for stabilizing the limb.

14. The device according to claim 13, in which said stabilization block is generally triangular in cross-section.

15. The device according to claim 13, in which said fasteners comprise hook-and-loop elements.

16. The device according to claim 13, in which said fasteners are located substantially at opposite ends of said strap.

17. The device according to claim 13, in which said strap is adhesively secured to said block.

* * * * *